US008784851B2

(12) United States Patent
Atkin et al.

(10) Patent No.: US 8,784,851 B2
(45) Date of Patent: Jul. 22, 2014

(54) TOPICAL FORMULATIONS CONTAINING SPOROPOLLENIN

(75) Inventors: Stephen Lawrence Atkin, Hull (GB); Stephen Thomas Beckett, Wigginton (GB); Grahame Mackenzie, Hull (GB)

(73) Assignee: University of Hull, Hull (GB)

( * ) Notice: Subject to any disclaimer, the term of this patent is extended or adjusted under 35 U.S.C. 154(b) by 1204 days.

(21) Appl. No.: 11/996,948

(22) PCT Filed: Jul. 27, 2006

(86) PCT No.: PCT/GB2006/002802
§ 371 (c)(1),
(2), (4) Date: Aug. 27, 2008

(87) PCT Pub. No.: WO2007/012857
PCT Pub. Date: Feb. 1, 2007

(65) Prior Publication Data

US 2008/0311213 A1 Dec. 18, 2008

(30) Foreign Application Priority Data

Jul. 28, 2005 (GB) .................................. 0515521.3
Aug. 10, 2005 (GB) .................................. 0516397.7

(51) Int. Cl.
*A61K 8/02* (2006.01)
*A61K 9/14* (2006.01)
*A61K 36/00* (2006.01)

(52) U.S. Cl.
USPC .......................................... 424/401; 424/489

(58) Field of Classification Search
CPC ........... A61K 8/11; A61K 8/975; A61K 9/48; A61K 9/4816; A61K 19/00
See application file for complete search history.

(56) References Cited

U.S. PATENT DOCUMENTS 4,917,892 A 4/1990 Speaker et al.
5,013,552 A 5/1991 Amer et al.
5,275,819 A 1/1994 Amer et al.
5,368,840 A 11/1994 Unger
5,508,021 A 4/1996 Grinstaff et al.
5,648,101 A 7/1997 Tawashi
6,156,330 A 12/2000 Tsukada et al.
6,342,255 B1 1/2002 De Gregorio
7,182,965 B2 2/2007 Maack
7,608,270 B2 10/2009 Beckett et al.
7,758,888 B2 * 7/2010 Lapidot et al. ................ 424/489
7,846,654 B2 12/2010 Atkin et al.
2004/0197405 A1 * 10/2004 Devane et al. ................ 424/469
2005/0002963 A1 1/2005 Beckett et al.
2005/0153862 A1 * 7/2005 Lau et al. ...................... 510/445
2005/0191374 A1 9/2005 Maack
2008/0112967 A1 5/2008 Feng et al.
2008/0188572 A1 8/2008 Atkin et al.
2009/0246125 A1 10/2009 Atkin et al.
2011/0002984 A1 * 1/2011 Atkin et al. .................. 424/451
2011/0117148 A1 5/2011 Atkin et al.
2013/0309298 A1 11/2013 Atkin et al.

FOREIGN PATENT DOCUMENTS

| | | |
|---|---|---|
| CN | 1 105 594 | 7/1995 |
| DE | 199 02 724 A1 | 7/2000 |
| DE | 102 16 772 A1 | 10/2003 |
| EP | 0 934 773 A2 | 8/1999 |
| GB | 0427520.2 | 12/2004 |
| GB | 0515521.3 | 7/2005 |
| GB | 0516397.7 | 8/2005 |
| GB | 0724550.9 | 12/2007 |
| GB | 0812513.0 | 7/2008 |
| JP | 59-116208 | 7/1984 |
| JP | 03-501485 | 4/1991 |
| JP | 04-341157 | 11/1992 |
| JP | 11-506451 | 6/1999 |
| WO | WO 96/38159 | 12/1996 |
| WO | WO 99/49063 | 9/1999 |
| WO | WO 01/80823 A2 | 11/2001 |
| WO | WO 02/055561 A1 | 7/2002 |
| WO | WO 03/078048 A2 | 9/2003 |
| WO | WO 03/094942 A1 | 11/2003 |
| WO | WO 2005/000280 A3 | 1/2005 |
| WO | WO2005000280 * | 1/2005 |
| WO | WO 2006/064227 | 6/2006 |
| WO | WO 2006/108595 | 10/2006 |
| WO | WO 2007/012856 | 2/2007 |
| WO | WO 2007/012857 | 2/2007 |
| WO | WO 2009/077749 | 6/2009 |
| WO | WO 2010/004334 | 1/2010 |

OTHER PUBLICATIONS

"Essential Oil." Encyclopedia Americana. Grolier Online, 2011. Web Oct. 27, 2011.*
US Office Action dated Feb. 6, 2007 issued in U.S. Appl. No. 10/877,042.
US Final Office Action dated Oct. 16, 2007 issued in U.S. Appl. No. 10/877,042.
US Office Action dated May 5, 2008 issued in U.S. Appl. No. 10/877,042.
US Office Action (Interview Summary) dated Oct. 16, 2008 issued in U.S. Appl. No. 10/877,042.
US Final Office Action dated Nov. 7, 2008 issued in U.S. Appl. No. 10/877,042.

(Continued)

*Primary Examiner* — Lakshmi Channavajjala
(74) *Attorney, Agent, or Firm* — Jennifer L. Wahlsten; Emily M. Haliday; Weaver Austin Villeneuve & Sampson LLP

(57) ABSTRACT

Topical formulation containing an active substance which is chemically or physically bound to, or encapsulated within, an exine shell of a naturally occurring spore. The active substance can be released from the exine shell on application to a living or non-living surface. The invention may be used to provide gradual release of an active substance over a period of time subsequent to application of the formulation to the surface.

18 Claims, No Drawings

(56) References Cited

OTHER PUBLICATIONS

US Office Action (Advisory Action) dated Dec. 22, 2008 issued in U.S. Appl. No. 10/877,042.
US Office Action (Interview Summary) dated Mar. 9, 2009 issued in U.S. Appl. No. 10/877,042.
US Notice of Allowance dated Jun. 22, 2009 issued in U.S. Appl. No. 10/877,042.
US Examiner Interview Summary dated Feb. 16, 2011 issued in U.S. Appl. No. 11/721,782.
US Office Action dated Mar. 17, 2011 issued in U.S. Appl. No. 11/721,782.
US Office Action dated Dec. 10, 2009 issued in U.S. Appl. No. 12/020,444.
US Office Action Final dated Apr. 26, 2010 issued in U.S. Appl. No. 12/020,444.
US Notice of Allowance dated Aug. 2, 2010 issued in U.S. Appl. No. 12/020,444.
PCT International Search Report dated Apr. 25, 2005 issued in PCT/GB2004/002775.
PCT International Preliminary Report on Patentability and Written Opinion dated Jan. 3, 2006 issued in PCT/GB2004/002775.
UK Search Report dated Dec. 15, 2003 issued in GB 0315019.0.
PCT Written Opinion dated Mar. 24, 2006 issued in PCT/GB2005/004824 (WO 2006/064227).
PCT International Search Report dated Mar. 27, 2006 issued in PCT/GB2005/004824 (WO 2006/064227).
PCT International Preliminary Report on Patentability dated Jun. 19, 2007 issued in PCT/GB2005/004824 (WO 2006/064227).
PCT International Search Report dated Oct. 13, 2006 issued in PCT/GB2006/002800 (WO 2007/012856).
PCT International Preliminary Report on Patentability and Written Opinion dated Jan. 29, 2008 issued in PCT/GB2006/002800 (WO 2007/012856).
PCT International Search Report dated Oct. 13, 2006 issued in PCT/GB2006/002802 (WO 2007/012857).
PCT International Preliminary Report on Patentability and Written Opinion dated Jan. 29, 2008 issued in PCT/GB2006/002802 (WO 2007/012857).
UK Search Report and Examination Opinion dated Dec. 7, 2005 issued in GB0516397.7.
Adamson et al., (Nov. 1983) "New applications of sporopollenin as a solid phase support for peptide synthesis and the use of sonic agitation" *International Journal of Peptide and Protein Research*, 22(5):560-564.
Ahlers et al., (Mar.-Apr. 2000)"The Nature of Oxygen in Sporopollenin from the Pollen of *Typha angustifolia* L.", *Journal of Biosciences*, 55(3-4):129-136.
Bohne et al., (2003) "Diffusion Barriers of Tripartite Sporopollenin Microcapsules Prepared from Pine Pollen", *Annals of Botany* 92:289-297.
Clark, Andy (Sep. /Oct. 2002) "Formulation of proteins and peptides for inhalation", *dds&s*, 2(3):73-77.
Crockford et al., (Dec. 2002/Jan. 2003) "Adaptive Aerosol Delivery (AAD™) technology: drug delivery technology that adapts to the patient", *dds&s*, 2(4):110-113.
Diego-Taboada et al., (Winter 2007) "Pollen: a Novel Encapsulation Vehicle for Drug Delivery", *Innovations in Pharmaceutical Technology*, pp. 63-66.
Fenyvesi et al., (Feb. 17, 2004) "Synthesis and characterization of tubular amphiphilic networks with controlled pore dimensions for insulin delivery", http://wost.wok.mimas.ac.uk:8000/C1W.cgi., 1 page.
Gregoriadis, Gregory (Dec. 2002/Jan. 2003) "Liposomes in drug and vaccine delivery", *dds&s*, 2(4):91-97.
Hamilton et al., (1984)"Survey for Prunus Necrotic Ringspot and Other Viruses Contaminating the Exine of Pollen Collected by Bees", *Canadian Journal of Plant Pathology*, 6(3):196-199, XP-002303282, (abstract only, 1 page).

Ivleva et al., (2005) "Characterization and discrimination of Pollen by Raman microscopy", *Analytical and Bioanalytical Chemistry*, 381(1):261-267.
Jorde et al., (1974) "ZUR Persorption Von Pollen UND Sporen Durch Die Intakte Darmschleimhaut", *Acta Allergologica*, 29:165-175 (no translation).
Odén et al. (1992) Demonstration of superoxide dismutase enzymes in extracts of pollen and anther of *Zea mays* and in two related products, Baxtin® and Polbax®, *Grana*, 31:76-80.
Penny, J. (Dec. 2002/Jan. 2003)"Bioavailability of orally delivered therapeutics: a biological perspective", *dds&s*, 2(4):100-102.
Polysciences, Inc., (Oct. 1999) "Sporopollenin Microparticles", *Technical Data Sheet* 281:1-2.
Reslow et al., (Dec. 2002/Jan. 2003)"Sustained-release of human growth hormone from PLG-coated starch microspheres", *dds&s*, 2(4):103-109.
Shaw et al., (Nov. 1, 1988) "The Use of Modified Sporopollenin from *Lycopodium clavatum* as a Novel Ion-or Ligand-Exchange Medium", *Reactive Polymers*, 9(2):211-217.
Smith, Ian (Dec. 2002/Jan. 2003) "Bioavailability, targeting and controlled release—the key to effective drug delivery?", *dds&s*, 2(4):89.
Soler et al., (1977) "Technical procedure for tagged pollen aerosols for the study of their penetration in the bronchial tree", *Clinical Respiratory Physiology*, France, 13(4):499-511.
"Sporomex Ltd: oral and respirable drug delivery", Page last modified on Mar. 2, 2005, www.sporomex.co.uk, 5 pages.
Stagg CM, Feather MS. (1973) "The Characterization of a Chitin-Associated $_D$-Glucan from the Cell Walls of *Aspergillus niger*", *Biochim Biophys Acta*, 320:64-72.
Stanley, R.G., Linskens H.F. (1974) Pollen: Biology, Biochemistry Management, New York, Springer-Verlag, 114-115, 179-181.
Volkheimer et al., (1967) "Le phénomène de la Persorption et son importance en Allergologie", *Maroc. Med.*, 47:626-633.
Weiner, M.L., (1998) "Intestinal Transport of Some Macromolecules in Food", *Fd Chem. Toxic*, 26(10):867-880.
Wiseman, Alan (Dec. 2002/Jan. 2003) "Targeted membrane-penetrating peptides: identify candidate drug-cargoes in silico?", *dds&s*, 2(4):114.
Wiseman, Alan (Dec. 2002/Jan. 2003) "Cell-Penetrating Peptides. Processes and Applications", *dds&s*, 2(4):115.
Wittborn et al., (1998) "Nanoscale Similarities in the Substructure of the Exines of *Fagus* Pollen Grains and *Lycopodium* Spores", *Annals of Botany* 82:141-145.
US Final Office Action dated Oct. 17, 2011 issued in U.S. Appl. No. 11/721,782.
US Office Action (Restriction Requirement) dated Feb. 9, 2012 issued in U.S. Appl. No. 12/747,484.
PCT International Search Report and Written Opinion dated May 15, 2009 issued in PCT/GB2008/004150.
UK Search Report dated Apr. 21, 2008 issued in GB 0724550.9.
Paunov et al. (2007) "Sporopollenin micro-reactors for in-situ preparation, encapsulation and targeted delivery of active components" *Journal of Materials Chemistry*, 17:609-612.
Twell, David, (2001) "Pollen: Structure, Development and Function", *Encyclopedia of Life Sciences*, John Wiley & Sons, Ltd., www.els.net,, [Retrieved from the Internet: URL:http://mrw.interscience.wiley.com/emrw/9780470015902/els/articlea0002039/current/pdf], 6 pages.
US Office Action dated May 4, 2012 issued in U.S. Appl. No. 12/747,484.
US Final Office Action dated Feb. 28, 2013 issued in U.S. Appl. No. 12/747,484.
US Office Action (Restriction Requirement) dated Dec. 11, 2012 issued in U.S. Appl. No. 13/001,767.
US Office Action dated Apr. 25, 2013 issued in U.S. Appl. No. 13/001,767.
US Final Office Action dated Nov. 6, 2013 issued in U.S. Appl. No. 13/001,767.
PCT International Search Report and Written Opinion dated Dec. 15, 2009 issued in PCT/GB2009/050813.
UK Search Report dated Nov. 26, 2008 issued in GB 0812513.0.
UK Search Report dated Oct. 26, 2009 issued in GB 0911927.2.

(56) References Cited

OTHER PUBLICATIONS

Barrier et al., (2010) "Viability of Plant Spore Exine Capsules for Microencapsulation," *Journal of Materials Chemistry*, This journal is © The Royal Society of Chemistry 2010, [Downloaded by University of Hull on Nov. 12, 2010], Published on Nov. 12, 2010 on http://pubs.rsc.orgldoi:10.1039/C0JM02246B, 7 pp.

Binks et al., (2005) "Naturally Occurring Spore Particles at Planar Fluid Interfaces and in Emulsions," *Langmuir*, 21(18):8161-8167.

Diego-Taboada et al., (2012) "Sequestration of Edible Oil from Emulsions Using New Single and Double Layered Microcapsules from Plant Spores," *Journal of Materials Chemistry*, 22:9767-9773.

Erdtman, G., (1960) "The Acetolysis Method, a Revised Description," *Svensk Botanisk Tidskrift*, 54(4):561-564.

Jordan et al.(Mar. 31, 2006) "Activity of bleach, ethanol and two commercial disinfectants against spores of *Encephalitozoon cuniculi*," Veterinary Parasitology, Elsevier Science, Amsterdam, NL, XP025025599,136(3-4):343-346.

* cited by examiner

US 8,784,851 B2

TOPICAL FORMULATIONS CONTAINING SPOROPOLLENIN

FIELD OF THE INVENTION

This invention relates to topical active substance-containing formulations and to new uses for naturally derived delivery systems.

BACKGROUND TO THE INVENTION

Many active substances need to be delivered topically, whether to human or animal skin (for instance, in the case of pharmaceutically active substances or cosmetics) or to an inanimate surface (for example, disinfectants and other household products, paints, varnishes, adhesives and the like). Such substances need to be formulated in a vehicle which is suitable both for their storage prior to use and for their subsequent topical delivery.

For some such products, it can be desirable to protect the active substance from environmental effects such as heat, moisture or in particular light or oxygen. Instead or in addition, such products may include volatile ingredients such as fragrances, the release of which may need to be minimised during periods of non-use.

Such aims can be achieved in part by encapsulating the relevant substance(s) in delivery vehicles such as liposomes or microcapsules. The preparation of such active-loaded delivery systems can often be complex, time consuming and expensive however. Problems can arise in ensuring that the encapsulating entities are sufficiently uniform in size and shape to ensure the resultant formulation meets quality control and regulatory standards and to provide homogeneity in active substance concentration. It can also be difficult to achieve adequately high active substance loadings in the encapsulating entities, without making those entities relatively large in size and in turn compromising the physical properties of the overall formulation.

It is moreover necessary in topical formulations to ensure that any encapsulated substances can be released to an adequate extent on application to the intended surface.

This is not always straightforward if the substance is also to be sufficiently well encapsulated as to protect it prior to the point of use.

From WO-2005/000280 it is known to use the exine coatings of naturally derived (typically plant) spores as delivery vehicles for pharmaceutical and dietetic substances. These coatings can be isolated from spores by successive treatments with organic solvents, alkali and acid so as to remove the lipid, carbohydrate, protein and nucleic acid components that may be attached to or contained within the exine shell. Enzymic methods have also been used to isolate the exine coating from other components of the spore.

Exine coatings take the form of essentially hollow capsules which can be impregnated or filled with, or chemically or physically bound to, another substance, for example as described in WO-2005/000280. They are known to be chemically and physically extremely stable.

The formulations disclosed in WO-2005/000280 are all pharmaceutical or dietetic dosage forms which are intended for systemic delivery, primarily oral or pulmonary although mention is also made of dermal and transdermal administration. The active ingredient is released when the exine is broken down, biochemically, within the body. In other words, these dosage forms are intended for absorption into the bloodstream followed by degradation of the exine coating to liberate the associated active substance. Such a release mechanism is clearly not suitable for local delivery of a substance. Where topical delivery is mentioned in WO-2005/000280, this is therefore in the context of transdermal delivery of systemic active substances.

It is an aim of the present invention to provide novel active substance-containing formulations which can help to provide an appropriate degree of protection for the active substance whilst also helping to achieve an appropriate degree of local release of the substance on topical administration.

STATEMENTS OF THE INVENTION

According to a first aspect of the present invention there is provided a topical formulation containing an active substance which is chemically or physically bound to, or encapsulated within, an exine shell of a naturally occurring spore.

"Naturally occurring" means that the spore is produced by a living organism, whether prokaryote or eukaryote and whether plant or animal. The spore (which term includes pollen grains and also endospores of organisms such as bacteria) may for instance be derived from a plant, or from a fungus, alga or bacterium or other micro-organism.

It has surprisingly been found that, although such exine shells can provide a protective wall around an encapsulated active, capable of protecting for instance against atmospheric effects such as light and oxygen, and preventing its premature release, they can nevertheless—if chosen from an appropriate source—release the encapsulated active on application of only moderate pressure. Thus, when a formulation according to the invention is applied topically, for instance with gentle rubbing, the active substance can be released from the exine shell directly to the intended site of action.

That such release is possible, even at relatively low pressures, and on a scale adequate to deliver an effective quantity of the active substance, could not have been predicted from previous work on exine delivery vehicles, such as the teachings of WO-2005/000280 which emphasised the physical integrity of the exine shell and relied instead on its biochemical degradation in order to release an associated active substance. Previous work with spore-derived exine shells has suggested that their strength and integrity might make it extremely difficult to achieve physical release of a substance encapsulated within them.

Exines of sporopollenin, for example, are known to be made of a very stable highly crosslinked polymer (G. Shaw, "The Chemistry of Sporopollenin" in *Sporopollenin*, J. Brooks, M. Muir, P. Van Gijzel and G. Shaw (Eds), Academic Press, London and New York, 1971, 305-348) which has survived for millions of years, morphologically intact, in sedimentary rocks (J. Brooks, "Some chemical and geochemical studies on sporopollenin" in *Sporopollenin*, J. Brooks, M. Muir, P. Van Gijzel and G. Shaw (Eds), Academic Press, London and New York, 1971, 351-407). In our own experiments on *Lycopodium clavatum* spores, it has been found necessary to apply pressures of around 376,700 hPa in order to squeeze out the natural oils contained within raw spores, and of 75,300 hPa to evacuate air from the empty spores. It is therefore surprising that such exines can allow encapsulated oils to be readily squeezed out by light rubbing between a finger and ordinary file paper, as will be described in the examples below.

Exine shells can be very effective at protecting an encapsulated active substance from atmospheric effects, in particular from light and/or oxygen, and therefore from premature degradation. The physical protection they provide can help reduce loss of the active substance by for instance evaporation, diffusion or leaching. It has also been found that in cases an exine can itself act as an antioxidant, rather than merely as a physical barrier to atmospheric oxygen, this effect being observable even when an active substance is outside of, rather than encapsulated within, the exine (see Examples 3 to 10 below). This can be of particular significance in the context of topical delivery, since on release of the active substance onto a surface, the substance will then be on the outside of the exine shell, yet can continue to benefit from a degree of oxidative protection.

Further advantages associated with the use of exine shells may be as described in WO-2005/000280, for example at pages 3 and 4 and in the paragraph spanning pages 5 and 6. In particular the exine shells prepared from any given organism tend to be very uniform in size, shape and surface properties, unlike typical synthetic encapsulating entities. There is however significant variation in spore size and shape, and in the nature of the pores in the exine shells, between different species, allowing a formulation according to the invention to be tailored dependent on the nature and desired concentration of the active substance, the site and manner of intended topical application, the desired active release rate, the likely storage conditions prior to use, etc. . . . .

It can also be possible to encapsulate relatively high quantities of an active substance within even a small exine shell. The combination of high active loadings, small encapsulant size and adequate protective encapsulation is something which can be difficult to achieve using other known encapsulation techniques, and yet can be extremely useful in the context of topical delivery where generally higher levels of active substance need to be applied to compensate for non-uniform application.

Finally, an exine shell is generally inert and non-toxic, the proteinaceous materials which can otherwise cause allergic reactions to pollens having been largely removed during the processes used to isolate the exine component. Sporopollenin for example, a component of many exine shells, is one of the most resistant naturally occurring organic materials known to man, and can survive very harsh conditions of pressure, temperature and pH as well as being insoluble in most organic solvents stable (see G. Shaw, "The Chemistry of Sporopollenin" in *Sporopollenin*, J. Brooks, M. Muir, P. Van Gijzel and G. Shaw (Eds), Academic Press, London and New York, 1971, 305-348).

The ready, and often inexpensive, availability of spore exines, together with their natural origin, also make them highly suitable candidates for active substance delivery vehicles.

In the context of the present invention a "topical" formulation is one which is suitable and/or adapted and/or intended for topical application, whether to a part of a living body or to an inanimate surface. It may be suitable and/or adapted and/or intended for topical application to areas of a living body such as the skin or other epithelia, the hair, the nails or the teeth, in particular to the skin. A living body may be either a plant or an animal, in particular an animal, and in the case of an animal may be either human or non-human.

An active substance may be any substance capable of producing an effect at the site of application. It may for example be selected from pharmaceutically active substances, herbicides, pesticides and pest control agents, plant treatment agents such as growth regulators, antimicrobially active substances, cosmetics (including fragrances), toiletries, disinfectants, detergents and other cleaning agents, adhesives, diagnostic agents and dyes. In general terms, any substance which can be used to treat a surface, in particular to alter its properties or those of any species associated with the surface, may be delivered using a formulation according to the invention.

In one embodiment of the invention, the active substance is a cosmetic substance. A cosmetic substance may for example be selected from makeup products (for example foundations, powders, blushers, eye shadows, eye and lip liners, lipsticks, other skin colourings and skin paints), skin care products (for example cleansers, moisturisers, emollients, skin tonics and fresheners, exfoliating agents and rough skin removers), fragrances, perfume products, sunscreens and other UV protective agents, self tanning agents, after-sun agents, anti-ageing agents and anti-wrinkle agents, skin lightening agents, topical insect repellants, hair removing agents, hair restoring agents and nail care products such as nail polishes or polish removers. A perfume product may comprise more than one fragrance.

In another embodiment of the invention, the active substance may be for use in a toiletry product. It may therefore be selected from soaps; detergents and other surfactants; deodorants and antiperspirants; lubricants; fragrances; perfume products; dusting powders and talcum powders; hair care products such as shampoos, conditioners and hair dyes; and oral and dental care products such as toothpastes, mouth washes and breath fresheners.

In yet another embodiment of the invention, the active substance is for use in a household product. It may for example be selected from disinfectants and other antimicrobial agents, fragrances, perfume products, air fresheners, insect and other pest repellants, pesticides, laundry products (eg, washing and conditioning agents), fabric treatment agents (including dyes), cleaning agents, UV protective agents, paints and varnishes.

In a further embodiment of the invention, the active substance is a pharmaceutically active substance, which includes substances for veterinary use. Pharmaceutically active substances suitable for topical delivery may for example be selected from substances for use in treating skin or skin structure conditions (for example acne, psoriasis or eczema), wound or burn healing agents, anti-inflammatory agents, anti-irritants, antimicrobial agents (which can include antifungal and antibacterial agents), vitamins, vasodilators, topically effective antibiotics and antiseptics.

A pharmaceutically active substance may be suitable and/or intended for either therapeutic or prophylactic use.

In particular the active substance may be selected from pharmaceutically active substances and cosmetic and toiletry substances. More particularly it may be a cosmetic or toiletry substance.

The active substance is suitably intended and/or adapted and/or suitable for topical delivery. It is preferably not a substance which is intended for and/or capable of systemic delivery, in particular via the skin. Suitably it is not a substance which is intended and/or adapted and/or suitable for ingestion, in particular by humans.

In certain cases it may be suitable for the active substance to be a substance other than an essential oil, or at least for it not to be an essential oil which is intended and/or suitable for systemic delivery to a living body.

In some cases it may be suitable for the active substance to be a substance other than a drug (at least a drug which is intended and/or suitable for systemic delivery) or a dietetic substance.

The active substance may comprise a volatile substance, in particular a fragrance. A formulation according to the invention can be particularly suitable for the delivery of such substances as the exine shell can help to inhibit release of any volatile components prior to use. This is also not necessarily predictable, bearing in mind that exine shells of naturally occurring spores are known to be porous. Nevertheless, they can in cases be capable of encapsulating volatile actives without undue loss to the atmosphere, as shown in Example 2 below.

The active substance may be sensitive to one or more external influences such as heat, light, oxygen or water. In particular it may be susceptible to oxidation, for example UV-induced oxidation, under ambient conditions.

The active substance may be a lipid or lipid-like substance (for example, an oil, fat or wax), and/or it may be lipophilic. It may be a liquid. In some cases it may be a non-polar substance.

It may be present in a secondary fluid vehicle such as a liquid vehicle, in particular a non-aqueous and more particularly a lipid vehicle, such as an oil. The active substance may therefore be present in the form of a solution or suspension, the term "suspension" including emulsions and other multiphase dispersions. A secondary vehicle may for example be a water-in-oil or oil-in-water-in-oil emulsion.

The active substance may itself be a naturally occurring substance or derived from a natural source, in particular a plant source.

A formulation according to the invention may contain more than one active substance. Two or more such substances may for example be co-encapsulated in the same exine shell. Instead or in addition, a formulation according to the invention may comprise two or more populations of active substance-containing exine shells, each chemically or physically bound to, or encapsulating, a different active substance.

Thus for example, a cosmetic formulation according to the invention might contain both a sunscreen and an insect repellant, or a sunscreen and a moisturiser, or a foundation or other skin colouring agent and a sunscreen.

This can also enable two or more active substances to be kept separate prior to use—of value for example if they are incompatible with one another or would interact in an undesirable manner—and then released together in situ at the intended point of use, on topical application.

In a formulation according to the invention, the active substance may be chemically or physically bound to, or encapsulated within, the exine shell. Suitably it is either physically bound to or encapsulated within the exine shell. More suitably it is at least partially encapsulated within the shell.

Suitable ways in which a substance may be chemically bound to an exine shell are described in WO-2005/000280, for example in the paragraph spanning pages 4 and 5, and at pages 14 to 22 and 24 to 32. They may involve chemical derivatisation of the exine shell so as to facilitate its chemical binding to the substance in question. Chemical binding may encompass covalent or other forms of chemical bond, for example hydrogen bonds, sulphide linkages, Van der Waals bonds or dative bonds.

Physical binding of an active substance to an exine shell may include for example adsorption (eg, involving hydrophobic/hydrophilic interactions) of the substance onto a surface (whether internal or external) of the shell.

Encapsulation of an active substance means that the substance is retained within the cavities that are inherently present in the exine shell wall and/or within the central cavity defined by the exine shell.

An active substance may be attached to an exine shell by more than one of the above described means; for example, it may be encapsulated within the shell and also chemically bound to it, or a portion of the substance may be adsorbed onto the outer surface of the shell whilst another portion is contained inside the shell.

An exine shell of a spore is the outer coating from around the naturally occurring ("raw") spore. It may consist in part or mainly of sporopollenin, and can be isolated from the other components of the spore such as the cellulosic intine layer, and proteinaceous and nucleic acid components, as explained above. It may be of a type described in WO-2005/000280, in particular at pages 4, 8 and 9 and in Example 1.

According to the present invention, the exine shell may be derived from any suitable naturally occurring spore, whether plant or animal in origin. In this context, the term "plant" is to be construed in its broadest sense, and embraces for example mosses, fungi, algae, gymnosperms, angiosperms and pteridosperms. Moreover the term "spore" is used to encompass not only true spores such as are produced by ferns, mosses and fungi, but also pollen grains, as are produced by seed-bearing plants (spermatophytes) and also endospores of organisms such as bacteria.

Suitable organisms from which such spores may be obtained include the following, the diameters of their spores being shown in the second column:

| | |
|---|---|
| *Bacillus subtilis* | 1.2 μm |
| *Myosotis* ("forget-me-not") | 2.4-5 μm |
| *Aspergillus niger* | 4 μm |
| *Penicillium* | 3-5 μm |
| *Cantharellus minor* | 4-6 μm |
| *Ganomerma* | 5-6.5 μm |
| *Agrocybe* | 10-14 μm |
| *Urtica dioica* | 10-12 μm |
| *Periconia* | 16-18 μm |
| *Epicoccum* | 20 μm |
| *Lycopodium clavatum* | 25 μm |
| *Lycopodium clavatum* | 40 μm |
| *Abies* | 125 μm |
| *Cucurbitapapo* | 200 μm |
| *Cuburbita* | 250 μm. |

Other spores from which exine shells can be extracted are disclosed in the publications referred to at page 8 of WO-2005/000280.

In a formulation according to the invention, the exine shell may have a diameter (which may be determined by scanning electron microscopy) of from 1 to 300 μm, suitably from 1 to 250 μm or from 3 to 50 μm or from 15 to 40 μm. Grass pollen-derived exines, and other exine shells of approximately 20 μm diameter, might also be expected to be suitable.

In some cases larger exine shells, for example of 30 or 40 μm diameter or greater, may be particularly suited as topical delivery agents as they are less likely to be persorbed into the bloodstream. Larger exine shells also have the advantage of allowing higher active substance loadings, but may compromise the texture and/or appearance of the overall formulation. Thus in some cases it may be suitable for the exine shells to have a diameter of 10 μm or less. Moreover when using larger shells, an associated active substance may be less homogeneously distributed throughout a formulation than when associated with a larger number of smaller shells. In general a minimum diameter of 4 μm might be preferable so as to be able to achieve reasonable active substance loadings. However there may be cases where the minimum diameter is suitably 60 μm or even more.

An exine shell may be obtained from a spore in known manner, for example by harsh treatment (eg, reflux) of the spore with a combination of organic solvent and strong acid and alkali. Suitable such methods are described for instance in WO-2005/000280 (see page 10) and in the examples below. Other less severe methods may also be employed, for instance enzyme treatment (S. Gubatz, M. Rittscher, A. Meuter, A. Nagler, R. Wiermann, Grana, Suppl. 1 (1993) 12-17; K. Schultze Osthoff, R. Wiermann, J. Plant Physiol., 131 (1987) 5-15; F. Ahlers, J. Lambert, R. Wiermann, Z. Naturforsch., 54c (1999) 492-495; C. Jungfermann, F. Ahlers, M. Grote, S. Gubatz, S. Steuernagel, I. Thom, G. Wetzels and R. Wiermann, J. Plant Physiol., 151 (1997) 513-519). Alternatively, high pressure may be used to press out the internal contents of a spore through the naturally occurring pores in its outer exine layer. These methods may be used to remove proteins or carbohydrates to obtain the exine shell that retains the largely intact morphology of the original spore.

For *Lycopodium clavatum*, for example, the resultant exine shell may consist entirely or essentially of sporopollenin, optionally with a proportion of other materials such as chitin, glucans and/or mannans. The majority of the protein from the original spore will have been removed.

In one embodiment of the invention, the exine shell may additionally contain all or part of the cellulose intine layer from the naturally occurring spore. This can be achieved if the spore is subjected to treatment with only organic solvent and alkali, and not with acid. Such base hydrolysis, for instance using potassium hydroxide, can ensure that proteinaceous components of the spore are removed, yet can allow at least a proportion of the original cellulosic intine to survive.

In one embodiment of the invention, the exine shell may be intact or substantially so. In other words, apart from the micro- or nanopores which are naturally present in the surfaces of such shells, it will provide a continuous outer wall defining an inner cavity into which an active substance can be loaded. The exine shell may however be broken or damaged in parts; the invention thus embraces the use of a fragment of a plant spore-derived exine shell as the delivery vehicle for the active substance, in particular in the case where the active substance is chemically or physically bound to the exine shell. Suitably however the exine shell is continuous over at least 50%, suitably at least 75 or 80 or 90%, in some cases at least 95 or 98 or 99%, of the surface area which an exine shell from the relevant species would have if intact. Such percentages may for instance be measured by viewing the shells using a confocal microscope.

The exine shell may be chemically modified, either to alter its properties (for example its solubility) or to target it to an intended site of administration (for example, to render it more surface-active), or to facilitate its attachment to the active substance. Suitable such chemical modifications, and methods for achieving them, are described in WO-2005/000280, in particular in the paragraph spanning pages 4 and 5, and at pages 14 to 22 and 24 to 32. The outside of the exine shell may for instance be modified by the (typically chemical) attachment of functional groups such as cationic and/or anionic groups (see WO-2005/000280 and also G. Shaw, M. Sykes, R. W. Humble, G. Mackenzie, D. Marsdan & E. Phelivan, *Reactive Polymers,* 1988, 9, 211-217), and/or functional groups which increase the affinity of the shell for a surface to which it is intended to be applied.

The active substance may be attached to, or encapsulated within, the exine shell using known techniques, again suitably as described in WO-2005/000280. In particular the exine shell may be impregnated with the active substance by immersing the shell in the active substance or a solution or suspension thereof. One or more penetration enhancing agents may be used, again as described in WO-2005/000280, to aid impregnation of the shell by the active substance. A reduced or increased pressure (with respect to atmospheric pressure) may instead or in addition be used to facilitate impregnation.

An active substance may be generated in situ on or within an exine shell, for instance from a suitable precursor substance already associated with the shell. For example, a precursor substance may be chemically or physically bound to, or encapsulated within, an exine shell, which is then contacted with a reactant substance which reacts with the precursor to generate the desired active substance. Such a method may be used to associate an exine shell with an insoluble active substance, starting from soluble precursor and reactant substances.

The exine shell may be loaded with any suitable quantity of the active substance, depending on the context of intended use. A formulation according to the invention may for example contain the active substance and exine shells at a weight ratio of from 0.1:1 to 33:1, such as from 0.1:1 to 15:1 or from 0.5:1 to 5:1. Larger exine shells may be needed in order to achieve larger active substance loadings.

The exine shell may be coated with a barrier layer for further protection of the associated active substance against atmospheric effects. This may be of particular use for the delivery of volatile active substances, and/or oxygen sensitive substances. Suitable coatings are solid or semi-solid under the normal storage conditions for the formulation (typically at room temperature) but may melt at a higher temperature (for instance, skin temperature) at which they are intended to be topically applied. Lipid coatings may be suitable for use in this way, examples including butters and other solid fats (eg, cocoa butter or hardened palm kernel oil), oils (eg, cod liver oil) and waxes (eg, carnuba wax or beeswax). Ideally the coating melts at or around skin temperature (cocoa butter is an example of such a material), and can therefore allow release of the active substance on topical application to the skin. Other potential coatings may be materials which can rupture on application of manual pressure, for example brittle solids such as shellac, or other materials which melt, break or otherwise change on topical application so as to allow release of the active substance. Gelatin may for example be a suitable coating material.

Other natural or synthetic coating excipients, including oligomers and polymers, may be used to protect the active substance in a formulation according to the invention. Vegetable-derived coating materials may be preferred.

Coatings may be applied to exine shells in known fashion, for instance by spraying, rolling, panning or dipping. Coatings do not necessarily have to be continuous around the entire outer surfaces of the shells.

A formulation according to the invention may contain one or more additional agents for instance selected from fluid vehicles, excipients, diluents, carriers, stabilisers, surfactants, penetration enhancers or other agents for targeting delivery of the exine shell and/or the active substance to the intended site of administration.

It may take the form of a lotion, cream, ointment, paste, gel, foam or any other physical form known for topical administration, including for instance a formulation which is, or may be, applied to a carrier such as a sponge, swab, brush, tissue, skin patch, dressing or dental fibre to facilitate its topical administration. It may take the form of a nasal spray or of eye or ear drops.

The formulation may alternatively take the form of a powder, for example when the active substance is a makeup product such as a blusher, eye shadow or foundation colour, or when it is intended for use in a dusting powder. Exine shells can be extremely efficient at absorbing liquids, in particular lipids, to result in an effectively dry product with all of the liquid encapsulated within the shells, as demonstrated in Example 11 below.

A second aspect of the present invention provides a product containing a formulation according to the first aspect. The product will itself be suitable and/or adapted and/or intended for topical application, as described above. The product may for example be selected from cosmetic products; toiletries (eg, bath products, soaps and personal care products); hair care products; nail care products; dental products such as toothpastes, mouth washes and dental flosses; household products (whether for internal or external use) such as surface cleaners, disinfectants, air fresheners, pest repellants and laundry and fabric treatment products; paints, inks, dyes and other colouring products; adhesive products; pharmaceutical products; agricultural and horticultural products; and explosives.

In particular a product according to the second aspect of the invention is selected from cosmetic products (which includes skin care products), toiletries, hair and nail care products and dental products.

In another embodiment of the invention, the product is a pharmaceutical (which includes veterinary) product.

Again, the product may contain more than one formulation according to the invention, each associated with a separate active substance.

The present invention can allow the co-administration of two or more materials, at least one of them being an active substance which is chemically or physically bound to, or encapsulated within, an exine shell and which is therefore released only at the point of topical application. For example, a product according to the second aspect of the invention may be a paint, containing an active substance such as a fragrance, air freshener, insect repellant or antifungal agent associated with an exine shell. On application of the paint to a surface, the active substance is released into the environment and/or onto the surface, due to the pressure used to apply the paint. In a similar manner, fragrances and/or other active substances may be released on topical application of any other product, for example a sun screen or other cosmetic substance.

A product according to the second aspect of the invention may thus include two or more substances, at least one of them being an active substance (in particular a fragrance) which is encapsulated within, or chemically or physically bound to, an exine shell of a naturally occurring spore. The other substance may itself be an active substance and/or may be encapsulated within, or chemically or physically bound to, an exine shell of a naturally occurring spore.

A third aspect of the invention provides a method for formulating an active substance for topical delivery, the method involving (a) preparing or providing an exine shell of a naturally occurring spore; and (b) encapsulating the active substance in the shell, or chemically or physically binding the active substance to the shell. The resultant product may thus be a formulation according to the first aspect of the invention. In particular, it may be a cosmetic formulation.

According to a fourth aspect, the invention provides a method for topically applying an active substance to a surface, the method involving (a) formulating the active substance with an exine shell of a naturally occurring spore in accordance with the third aspect of the invention; and (b) applying the resultant formulation to the surface. The formulation is preferably applied with gentle pressure, for instance with gentle rubbing (as with the fingertips) or brushing.

The method may be carried out in order to provide gradual release of the active substance over a period of time subsequent to application of the formulation to the surface.

In one embodiment of this fourth aspect of the invention, the surface is a living surface such as human or animal (in particular human) skin. In another embodiment, the surface is an inanimate surface, for example a household or work surface, an item of apparatus such as an implement or a textile item such as of clothing or bedding. An item treated in this way may be intended for subsequent contact with a living body—it may for example be a contact lens, hearing aid, implant, prosthesis or stent.

When the formulation is applied to a living surface, this may be done for purely non-therapeutic (eg, cosmetic) purposes or to deliver a pharmaceutically active substance. The method of the fourth aspect of the invention may therefore embrace a method of treatment of a human or animal patient, which method involves topically applying to a surface of the patient's body a formulation according to the first aspect of the invention which contains a therapeutically or prophylactically effective amount of a pharmaceutically active substance.

It has been found that an active substance may be released from a formulation according to the invention by the application of gentle pressure—such as rubbing or squeezing—of a level similar to that typically used when a pharmaceutical or cosmetic preparation is topically applied to the skin with the fingers. The active substance can moreover be released gradually, either by applying gradually increasing pressure or more particularly by a series of successive applications of pressure. In this way, the present invention may be used to allow controlled release of an active substance. For example, a fragrance or insect repellant or anti-irritant contained within a topical formulation may be released in a series of stages by repeated rubbing of the treated area; the user may therefore release further amounts of the relevant substance whenever desired.

Thus, the method of the fourth aspect of the invention may involve, subsequent to step (b), one or more further applications of pressure to the treated surface, so as to effect a gradual (typically step-wise) release of the active substance.

The initial application of pressure may in some cases be sufficient to rupture a coating present around the exine shell, and thus to allow a gradual leakage of the associated active substance over a period of time, again assisting in the controlled release of the active after its topical application.

A fifth aspect of the invention provides an exine shell of a naturally occurring spore for use as a topical delivery vehicle for a pharmaceutically active substance.

A sixth aspect provides the use of an exine shell of a naturally occurring spore in the manufacture of a medicament for topical application to a human or animal body.

A seventh aspect provides the use of an exine shell of a naturally occurring spore as a topical delivery vehicle for an active substance. The active substance may be a substance other than a pharmaceutically active substance.

According to an eighth aspect, the invention provides the use of an exine shell of a naturally occurring spore for the dual purposes of (a) protecting an active substance prior to its topical delivery and (b) releasing the active substance on topical application to a surface. As described above, it may be used for the purpose of facilitating a controlled release of the active substance over a period of time following initial application to the surface.

The exine shell may additionally be used as an antioxidant, prior to and/or during and/or subsequent to application of the active substance.

A ninth aspect of the invention provides the use of an exine shell of a naturally occurring spore as a delivery vehicle for an active substance, wherein the exine shell also contains a cellulosic intine material from the spore. It has been found that such exine/intine combinations can be useful delivery vehicles for a range of substances. They can be prepared by subjecting a spore to base hydrolysis, for instance using potassium hydroxide, so that although proteinaceous components of the spore are removed, at least a proportion of the original cellulosic intine layer survives.

Retention of the intine has in some cases been found to alter the active substance releasing and/or antioxidant properties of the exine shell, as shown in the examples below.

According to a tenth aspect, the invention therefore provides a formulation containing an active substance which is chemically or physically bound to, or encapsulated within, an exine shell of a naturally occurring spore, wherein the exine shell also contains a cellulosic intine material from the spore.

Throughout the description and claims of this specification, the words "comprise" and "contain" and variations of the words, for example "comprising" and "comprises", mean "including but not limited to", and do not exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Preferred features of each aspect of the invention may be as described in connection with any of the other aspects.

Other features of the present invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith.

Moreover unless stated otherwise, any feature disclosed herein may be replaced by an alternative feature serving the same or a similar purpose.

The present invention will now be described by means of the following non-limiting examples.

EXAMPLES

The following experiments demonstrate the suitability of spore-derived exine shells for the topical delivery of active substances, in particular lipid-based substances such as cosmetics.

The exine shells used were extracted from the spores of *Lycopodium clavatum* L. (common club moss), which can be purchased for example from Unikem, Post Apple Scientific, Fluka and Tibrewala International. Both 25 and 40 μm spores were tested, the 40 μm being derived from a sub-species or genetic variant of the plant. The former have a reticulated outer surface whilst the latter appear smoother and rounder. Both are believed to have an exine shell approximately 1.5 μm thick.

The exine shells were isolated from other components present in the spores (in particular the proteinaceous components) using the extraction procedures described below. Samples designated "AHS" were subjected to acid hydrolysis with phosphoric acid following base hydrolysis with potassium hydroxide, whereas those designated "BHS" were subjected only to base hydrolysis with potassium hydroxide. The BHS samples therefore comprised not only the exine shell but also a proportion of the cellulosic intine layer.

Firstly, the raw spores were suspended in acetone and stirred under reflux for 4 hours. For this, 250 g of the spores were dissolved in 750 ml of acetone, and refluxed for 4 hours in a 2 liter round bottomed flask fitted with two double surface Liebigs condensers (20 cm-4 cm). The resultant defatted spores (DFS) were then filtered (porosity grade 3) and dried overnight in air.

To produce the base-hydrolysed (BHS) exines, the defatted spores (DFS) were suspended in 6% w/v aqueous potassium hydroxide and stirred under reflux (conditions as described above) for 6 hours. After filtration (porosity grade 3), this operation was repeated with a fresh sample of the potassium hydroxide solution. Again the suspension was filtered (grade 3) and the resultant solid washed with hot water (three times) and hot ethanol (twice). It was then refluxed in ethanol (conditions as described above) for 2 hours, filtered (grade 3) and dried overnight in air. Subsequently it was thoroughly dried in an oven at 60° C.

To produce the acid-hydrolysed (AHS) exines, the defatted spores were suspended in 85% v/v ortho-phosphoric acid (750 ml), and stirred under reflux (conditions as described above) for 7 days. The solid was then filtered (porosity grade 3), washed with water (5 times, 250 ml), acetone (5 times, 250 ml), ethanol (once, 250 ml), 2M sodium hydroxide (once, 250 ml), water (5 times, 250 ml), acetone (once, 300 ml) and ethanol (once, 300 ml). It was then dried in an oven at 60° C.

Both the BHS and the AHS products contained essentially no nitrogen (assessed by combustion elemental analysis and by IR spectroscopy), indicating removal of proteins and nucleic acids and hence potentially allergenic components of the original spores. They were observed by scanning electron microscope and confocal electron microscopy to be essentially hollow capsules, free of the original inner sporoplasm.

Unless otherwise stated, the exine shells were loaded with oil using the following procedure. The oil was heated to between 40 and 60° C. and mixed with a few drops of ethanol. The relevant exine shells were then added to the resulting emulsion to form a homogeneous mixture. This was subjected to vacuum (30 hPa) for 1 to 2 hours to facilitate impregnation of the shells with the oil. Samples were prepared using 1 g of oil in each case, altering the quantity of exine in order to achieve different loadings.

Example 1

Release of Encapsulated Active

This example illustrates the effectiveness of exine shells in delivering an encapsulated agent. This in turn shows their potential as delivery vehicles for substances which need to be applied topically to a surface.

Samples of echium oil-loaded exine shells were prepared as described above. The exines used were as follows:

A AHS, particle diameter 40 μm.
B AHS, particle diameter 25 μm.
C BHS, particle diameter 40 μm.
D BHS, particle diameter 25 μm.

For each type of exine shell, various samples were prepared, having oil:exine shell weight ratios of approximately 1:1, 2:1, 3:1, 4:1 and 5:1.

Each sample was subjected to the following test. Approximately 20 mg of the sample was gently rubbed over a pre-weighed paper sheet (Impega® white paper) using the finger tips. The same sample was then removed to a second pre-weighed sheet of paper and rubbed again, this being repeated a third and fourth time. After each rubbing, the paper sheet was weighed to determine the amount of oil on it, from which was calculated the amount of oil remaining in the sample. Each experiment was conducted in triplicate and the results averaged.

The averaged results are shown in Tables 1 to 4 below.

TABLE 1

Sample A

| Oil loading | Oil remaining in the exine sample (% w/w) | | | |
|---|---|---|---|---|
| | After 1$^{st}$ rubbing | After 2$^{nd}$ | After 3$^{rd}$ | After 4$^{th}$ |
| 1:1 | 76 | 66 | 63 | 61 |
| 2:1 | 74 | 64 | 58 | 54 |
| 3:1 | 64 | 50 | 42 | 35 |
| 4:1 | 64 | 44 | 31 | 26 |
| 5:1 | 62 | 40 | 29 | 24 |

TABLE 2

Sample B

| Oil loading | Oil remaining in the exine sample (% w/w) | | | |
|---|---|---|---|---|
| | After 1$^{st}$ rubbing | After 2$^{nd}$ | After 3$^{rd}$ | After 4$^{th}$ |
| 1:1 | 77 | 66 | 55 | 46 |
| 2:1 | 61 | 44 | 37 | 33 |
| 3:1 | 64 | 49 | 43 | 31 |
| 4:1 | 44 | 21 | 6 | 4 |
| 5:1 | 40 | 26 | 7 | 2 |

TABLE 3

Sample C

| Oil loading | Oil remaining in the exine sample (% w/w) | | | |
|---|---|---|---|---|
| | After 1$^{st}$ rubbing | After 2$^{nd}$ | After 3$^{rd}$ | After 4$^{th}$ |
| 1:1 | 68 | 57 | 48 | 42 |
| 2:1 | 76 | 60 | 53 | 46 |
| 3:1 | 62 | 43 | 33 | 29 |
| 4:1 | 54 | 42 | 34 | 29 |
| 5:1 | 51 | 38 | 34 | 27 |

TABLE 4

Sample D

| Oil loading | Oil remaining in the exine sample (% w/w) | | | |
|---|---|---|---|---|
| | After 1$^{st}$ rubbing | After 2$^{nd}$ | After 3$^{rd}$ | After 4$^{th}$ |
| 1:1 | 89 | 84 | 81 | 81 |
| 2:1 | 79 | 67 | 64 | 63 |
| 3:1 | 69 | 55 | 51 | 47 |
| 4:1 | 57 | 44 | 43 | 42 |
| 5:1 | 52 | 39 | 32 | 28 |

These results show firstly that the encapsulated oil can be readily removed from the exine shells by the application of only gentle pressure, of the type that might be used when manually applying an active substance-containing formulation to the skin. After only four gentle squeezes, relatively large amounts of oil have been extracted.

It is believed that the encapsulated oil is effectively "squeezed out" of the exine shells, as though the shells were acting as sponges. Nevertheless, without the application of pressure the shells retain the oil, only releasing it when pressure is applied, making them particularly suitable as delivery agents for topical formulations. Prior to application, the encapsulated ingredient is protected from atmospheric effects, for example as illustrated in Examples 2 and 3 below.

The release effect is greater for the exine shells containing higher oil loadings. This may be due to the mathematical lack of space (relatively speaking) for the encapsulated oil at higher loadings, and may indeed have been observed because a proportion of the oil was not actually encapsulated. At an oil loading of 1:1, at which all of the oil is likely to be encapsulated, it can be seen that the 40 μm BHS exine shells lead to the most rapid release, followed by the 25 μm AHS sample. This result is not necessarily predictable, as (a) the intine layer might be expected to help retain the oil and (b) smaller particles, being relatively more full of oil at any given loading, might be expected to yield a faster release.

These results also show that a staged release of the encapsulated oil may be achieved by the application of a series of gentle squeezes. This makes a formulation according to the invention suitable for the controlled release of topical active substances, as it may be applied to a surface and then subsequently, on application of gentle pressure, caused to release a further quantity of the encapsulated active.

The fact that release rates vary depending on exine particle size, oil loading and whether or not the cellulose intine is present indicates that a delivery system according to the invention can be readily tailored to provide a desired release rate for an active substance. The origin of the exine shell (ie, the plant from which it derives) is also expected to influence the rate of release of an associated active substance.

Example 2

Protection of Volatile Actives

This experiment assessed the evaporation rate of a volatile active substance from within spore-derived exine shells.

Exine shells (AHS, 40 μm diameter) were prepared as described above, and loaded with butanol. Alcohols are not only volatile substances, but are also commonly used as diluents in topical formulations such as cosmetics. Impregnation was achieved by "passive contact", ie, by mixing the alcohol with the exine shells at room temperature and pressure and allowing the fluid to permeate into the shells.

Sample A contained 2 ml of neat butanol, as a control; sample B contained 2 ml of butanol encapsulated in 1 g of exine shells.

Each sample was spread on a Petri dish and weighed at 5 minute intervals in order to measure the time taken for all of the encapsulated alcohol to evaporate. All experiments were conducted in triplicate.

The results of these tests are shown in Table 5 below. The half life quoted in each case is a theoretical, calculated indication of the time taken for half the amount of encapsulated alcohol to evaporate.

TABLE 5

| Sample | Evaporation time (min) | Half life (min) |
|---|---|---|
| A | 200 | 61 |
| B | 300 | 115 |

Table 5 shows that encapsulation of a volatile alcohol within an exine shell can considerably inhibit its release by evaporation. A protective coating, for example a lipid coating layer, could be applied to the shells in order to slow evaporative loss yet further and thus to protect volatile active substances in topical formulations according to the invention. Release could still be readily achieved at the desired time, merely by application of the shells to a surface with gentle pressure, as illustrated in Example 1, in particular using a coating such as cocoa butter which is liquid at the temperature of a surface such as human skin.

Example 3

Protection Against Oxidation

The following example, together with Examples 4 to 10 below, demonstrates the surprising ability of a spore-derived exine shell to act as an antioxidant, and its suitability therefore to preserve oxygen-sensitive substances both prior to, during and after their topical application.

To test the stability of an exine shell-encapsulated oil to UV light, 25 μm AHS exine shells were loaded with either sunflower, rapeseed or soybean oil at an oil:exine weight ratio of 1:1.

The exine shells were loaded with the relevant oil using the procedure outlined above. Each sample was then spread out on a sheet of paper and irradiated with UV light for 2 hours, using a Philips™ Original Home Solaria type HB 171/A, 220-230 volt, 50 Hz, 75 watts, with four Philips™ CLEO 15 W UV type 30 bulbs. The lamp was held at a distance of 13 cm from the samples.

As controls, unloaded exine samples were subjected to the same treatment.

Following irradiation, the peroxide value (PV) of each sample was determined by titration. For this, the sample was dissolved by stirring in chloroform (10 ml), and acetic acid (15 ml) was added together with a saturated aqueous potassium iodide solution (1 ml). This mixture was shaken in a stoppered flask for 1 minute and set aside, away from the light, for exactly 5 minutes at room temperature. It was then diluted with 75 ml of distilled water and titrated against aqueous sodium thiosulphate (0.01 N), using starch solution as indicator. From this the peroxide value, which is a measure of the amount of active oxygen contained in the sample, could be calculated—degradation of the fat by oxygen generates peroxides, which when treated as described above yield molecular iodine, which is detectable by its reaction with starch to generate colourless sodium iodide. PVs were therefore determined using a standard procedure (IUPAC method 2.500).

The peroxide value of a lipid sample provides an indication of the extent to which the lipid has been degraded to peroxides, and hence of its rancidity. The higher the peroxide value, the more rancid the lipid, and thus the greater the degree of oxidation which it has undergone.

The results are shown in Table 6 below.

TABLE 6

| Oil | Loaded/unloaded exine sample | Exposure to UV (hours) | Peroxide value (PV) (meq/kg) |
|---|---|---|---|
| Sunflower | Unloaded | 0 | 25.3 |
|  | Unloaded | 2 | 31.2 |
|  | Loaded | 2 | 24.9 |
|  | Loaded | 2 | 27.7 |
| Rapeseed | Unloaded | 0 | 5.4 |
|  | Unloaded | 0 | 5.0 |
|  | Unloaded | 2 | 36.4 |

TABLE 6-continued

| Oil | Loaded/unloaded exine sample | Exposure to UV (hours) | Peroxide value (PV) (meq/kg) |
|---|---|---|---|
|  | Loaded | 0 | 8.2 |
|  | Loaded | 2 | 5.7 |
| Soybean | Unloaded | 0 | 10.2 |
|  | Unloaded | 2 | 20.6 |
|  | Loaded | 2 | 12.2 |

The Table 6 results show that encapsulation of the oils in the exine shells significantly reduces their oxidation rate on exposure to UV light. This makes the exine shells highly suitable for use as vehicles for oxygen- and/or UV-sensitive substances, in particular lipids, which can then be protected against oxidation during their storage prior to use, and indeed during and after their topical application.

Example 4

Stability to UV Light (2)

Duplicate samples were prepared in which echium oil (0.5 g) was added to 25 μm AHS exine shells (0.125 g) to form a homogeneous mixture with an oil:exine weight ratio of 4:1. Unlike in Example 3, the mixture was not subjected to vacuum in order to impregnate the shells with the oil; the oil and exine shells were therefore present as a simply physical mixture, with the majority of the oil outside of the shells.

The samples were irradiated with UV light, and their peroxide values determined both before and after irradiation, as described in Example 3. Again, neat echium oil was used as a control.

The results are shown in Table 7.

TABLE 7

| Oil:exine weight ratio | Exposure to UV (hours) | Peroxide value (meq/kg) |
|---|---|---|
| 1:0 | 0 | 9.0 |
| 1:0 | 0 | 8.5 |
| 1:0 | 2 | 110.1 |
| 1:0 | 2 | 130.3 |
| 4:1 | 2 | 10.1 |
| 4:1 | 2 | 12.5 |

Within experimental error, these data show that the exine shells protect the echium oil to a very significant extent against UV light. This illustrates the natural antioxidant properties of the shells, since in this case most of the oil is likely to be surrounding the exine shells rather than encapsulated within them.

Example 5

Stability Against Aerial Oxidation (1)

This experiment evaluated the protective properties of exine shells against aerial oxidation. Oxidative induction times (OITs), as a measure of the effect of ambient oxygen on oil rancidity, were determined using a Metrohm™ 743 Rancimat machine, version 1.0 SRI, with an air flow rate of 20 l/hour and an operating temperature of 50° C. The Rancimat determines the oxidative stability of in particular edible oils and fats, according to the AOCS Air Oxidation Method (AOM-AOCS Cd 12b-92).

All materials—including oils, fats, fatty acid amides and other fatty acid derivatives—have a degree of innate resistance to oxidation. The level of this natural antioxidancy depends on the material itself and any additives it contains, as well as on its prior treatment. Oxidation tends to proceed slowly until the innate resistance is overcome, at which point it accelerates rapidly. The OIT is the length of time before the onset of such acceleration. It is the time limit after which the material under test is generally considered to be rancid.

Using a Rancimat, a stream of filtered and dried air is passed through a sample which is held in a heating block at a predetermined temperature. The effluent air leaving the sample is then bubbled through deionised water, the electrical conductivity of which is constantly measured via a conductivity measuring cell. The sample as it oxidises produces volatile organic compounds including carboxylic acids, predominantly formic acid; the presence of such species in the effluent air produces a corresponding change in conductivity of the initially deionised water. A graph is produced showing the change in conductivity with time, from which the OIT (defined as the point of maximum change in the oxidation rate) can be automatically derived by the Rancimat by reference to the maximum in the second derivative of the conductivity with respect to time.

Three samples were prepared, each in duplicate: fresh echium oil, mixed into glass wool; empty exine shells (obtained as described above) mixed into glass wool; and echium oil loaded into 40 μm AHS exine shells. The oil:exine weight ratio in the latter case was 0.5:1. Confocal electron microscopy showed that in the third sample, the oil was encapsulated by the exine shells.

Air was blown below a loose dispersion of each sample, so as to ensure a large contact surface area. The samples were then assessed using the Rancimat machine, as described above. The results are shown in Table 8.

TABLE 8

| Tube | Glass wool (g) | Product | Oil (g) | | Oil:exine weight ratio | Induction time (hours) |
|---|---|---|---|---|---|---|
| 1 | 1.5 | Empty exines | 0.5 | 0.0 | 0:1 | >190 |
| 2 | 1.5 | | 0.5 | 0.0 | 0:1 | >190 |
| 3 | 1.5 | Oil loaded | 1.5 | 0.5 | 0.5:1 | >190 |
| 4 | 1.5 | exines | 1.5 | 0.5 | 0.5:1 | >190 |
| 5 | 1.5 | Echium oil | 0.5 | 0.5 | 1:0 | 45 |
| 6 | 1.5 | | 0.5 | 0.5 | 1:0 | 50 |

The Table 8 data show that the exine-encapsulated oil is significantly more resistant to aerial oxidation, and hence significantly more stable. This implies a protective effect due to the exine shell. The protection is likely to be more than simply the shell acting as a physical barrier to the ingress of oxygen, as spore-derived exine shells are known to be at least partially porous.

Example 6

Stability Against Aerial Oxidation (2)

Example 5 was repeated, but using 25 μm AHS exine shells and replacing the encapsulated oil sample with a physical mixture of echium oil and exine shells. The physical mixture contained an oil:exine weight ratio of 5:1 (0.5 g of oil to 0.1 g of ex

TABLE 11

40 μm AHS

| Oil | Loaded/unloaded exine sample | Exposure to UV (hours) | Peroxide value (PV) (meq/kg) |
|---|---|---|---|
| Echium | Unloaded | 0 | 13.5 |
|  | Unloaded | 2 | 67.9 |
|  | Loaded | 0 | 20.9 |
|  | Loaded | 2 | 36.7 |
| Cod liver | Unloaded | 0 | 4.5 |
|  | Unloaded | 2 | 18.3 |
|  | Loaded | 0 | 8.5 |
|  | Loaded | 2 | 8.7 |

TABLE 12

25 μm BHS

| Oil | Loaded/unloaded exine sample | Exposure to UV (hours) | Peroxide value (PV) (meq/kg) |
|---|---|---|---|
| Echium | Unloaded | 0 | 13.5 |
|  | Unloaded | 2 | 67.9 |
|  | Loaded | 0 | 13.0 |
|  | Loaded | 2 | 17.5 |
| Cod liver | Unloaded | 0 | 4.5 |
|  | Unloaded | 2 | 18.3 |
|  | Loaded | 0 | 4.5 |
|  | Loaded | 2 | 7.3 |

TABLE 13

40 μm BHS

| Oil | Loaded/unloaded exine sample | Exposure to UV (hours) | Peroxide value (PV) (meq/kg) |
|---|---|---|---|
| Echium | Unloaded | 0 | 13.5 |
|  | Unloaded | 2 | 67.9 |
|  | Loaded | 0 | 0.0 |
|  | Loaded | 2 | 0.0 |
| Cod liver | Unloaded | 0 | 4.5 |
|  | Unloaded | 2 | 18.3 |
|  | Loaded | 0 | 0.0 |
|  | Loaded | 2 | 0.0 |

These data confirm that encapsulation of the oils into exine shells can significantly reduce their oxidation rate on exposure to UV light.

The results are particularly marked for the 40 μm BHS, which appears to completely protect both oils from oxidation. Moreover, the exine shells in this case appear to "clean up" the oils, reducing their peroxide values even before UV irradiation: this suggests that this BHS is contributing a significant antioxidant effect irrespective of its ability to screen the oil from applied UV light, and that it may even in certain circumstances be capable of removing any previously accrued rancidity.

Example 8

"Clean Up" of Rancid Oils (1)

Example 7 was repeated using cod liver oil, 40 μm exine shells (both AHS and BHS) and an exine:oil weight ratio of 0.5:1, ie, a much higher oil loading. The results are shown in Table 14 below.

TABLE 14

| Sample | PV (meq/kg) before irradiation | PV (meq/kg) after irradiation |
|---|---|---|
| Neat cod liver oil | 4.5 | 18 |
| 40 μm AHS + oil | 10 | 13 |
| 40 μm BHS + oil | 0 | 0 |

Again this demonstrates the ability of the BHS (exine+intine) shells to "clean up" rancidity, the peroxide value for the (exine+oil) sample being lower even than that for the original oil sample.

Example 9

Clean Up of Rancid Oils (2)

Example 8 was repeated, but using an echium oil that already had a peroxide value of 20.5 meq/kg, ie, which was already turning rancid.

The results, prior to irradiation, are shown in Table 15.

TABLE 15

| Sample | Exine:oil weight ratio | PV (meq/kg) before irradiation |
|---|---|---|
| Neat echium oil | 0:1 | 20.5 |
| 40 μm AHS + oil | 1:1 | 25.5 |
| 40 μm AHS + oil | 0.5:1 | 26.5 |
| 40 μm BHS + oil | 1:1 | 3 |
| 40 μm BHS + oil | 0.5:1 | 8.5 |

Again these data demonstrate the surprising ability of the 40 μm BHS (ie, exine/intine combination) to "clean up" an already rancid oil. The peroxide value of the original oil sample is significantly reduced after encapsulation in the exine shells. The higher the proportion of exine shells, the greater the effect.

Example 10

Stability Against Aerial Oxidation (3)

Example 5 was repeated but using cod liver oil.

40 μm exine shells (both AHS and BHS) were used for these tests, and were loaded with cod liver oil at oil:exine weight ratios of 1:1, 3:1 and 5:1. Each sample was wedged into the middle of a sample tube between two glass wool wads. A capillary tube was passed through the resulting plug, ensuring that no oil ran down the bottom of the tube. These tubes were then inserted into the heating blocks of the Rancimat machine and air flow commenced.

The results are shown in Table 16 below.

TABLE 16

| Sample | Oil:exine ratio (w/w) | OIT (hours) |
|---|---|---|
| Cod liver oil | 1:0 | 56 |
| Oil:BHS | 5:1 | 59 |
| Oil:BHS | 3:1 | >120 |
| Oil:BHS | 1:1 | >120 |
| Oil:AHS | 5:1 | 73 |
| Oil:AHS | 3:1 | >120 |
| Oil:AHS | 1:1 | >120 |

The Table 16 data again show that the exine-encapsulated oil is significantly more resistant to aerial oxidation, and hence significantly more stable.

The higher the oil loading, the lower the protective effect, since more of the oil is likely to be outside of the exine shells and/or only loosely associated with them (encapsulated oil will benefit not only from the natural antioxidancy of the exine shells but also from physical protection from the air).

Example 11

High Active Substance Loadings

Oil was stirred with 25 μm AHS exine shells to form a homogeneous mixture which was then subjected to vacuum (30 kPa) for 2 hours in order to impregnate the shells with the oil. The oils used were soybean oil, sunflower oil, echium oil and rapeseed oil, each up to 3 g per gram of exine shells and in the case of the cod liver oil up to 3.5 g per gram of exine shells.

It was found that even at these relatively high loadings, the oil-loaded exine shells behaved as powders, confirming effective encapsulation of the oils. This was further confirmed by confocal microscopy. It demonstrates one of the advantages of using spore-derived exine shells as delivery vehicles for active substances. It also shows the suitability of the shells as vehicles in topical powder formulations, for instance for delivery of cosmetic substances such as dusting powders and makeup, or of cleaning products or laundry products.

At loading levels at and above 5 g of oil per gram of exine shells, the samples behaved more as pastes, indicating that a significant proportion of the oil was then outside of the exine shells. Such formulations might be suitable for application as a cream or ointment, for example. At loading levels at and below 2 g of oil per gram of exine shells, the powders were fine, free flowing powders and reasonably dry to the touch.

Example 12

Topical Cosmetic Formulation

A topical cosmetic formulation may be prepared, according to the present invention, using spore-derived exine shells for instance as prepared in the examples above, and loading them with a cosmetic substance such as a sun screen. The loaded exine shells may then be suspended in any suitable vehicle, many of which are known for use in cosmetic and indeed other types of topical formulation. The resultant formulation may be a lotion, cream or gel or have any other suitable form. It may be applied to the skin using the fingertips, at which point at least a proportion of the encapsulated sun screen will be released onto the skin surface. Further quantities of the sun screen may be released subsequently by gently rubbing the treated area.

Such a formulation may contain exine shells loaded with two or more different cosmetic substances (one of which may, for example, be a fragrance), which are then released together on topical application.

The invention claimed is:

1. A topical formulation which takes the form of a lotion, cream, ointment, paste, gel, foam or powder, the formulation comprising an active substance which is chemically or physically bound to, or encapsulated within exine shells of naturally occurring spores, wherein the majority of the exine shells are at least 90% intact, further wherein the active substance can be released by one or repeated applications of manual pressure to the exine shells, and wherein the active substance is not a substance that is intended for and/or capable of systemic delivery.

2. A topical formulation according to claim 1, wherein the active substance is selected from pharmaceutically active substances, antimicrobially active substances, cosmetic substances, toiletry substances, disinfectants, detergents and other cleaning agents, adhesives, and dyes.

3. A topical formulation according to claim 2, wherein the active substance is selected from pharmaceutically active substances, cosmetic substances and toiletry substances.

4. A topical formulation according to claim 1, wherein the active substance comprises a volatile substance.

5. A topical formulation according to claim 4, wherein the active substance comprises a fragrance.

6. A topical formulation according to claim 1, wherein the active substance comprises a lipid or lipid-like substance, or is present in a lipid vehicle.

7. A topical formulation according to claim 1, which comprises two or more populations of active substance-containing intact or substantially intact exine shells, each chemically or physically bound to, or encapsulating, a different active substance.

8. A topical formulation according to claim 1, wherein the active substance is at least partially encapsulated within the exine shells.

9. A topical formulation according to claim 1, wherein the majority of exine shells have a diameter of from 1 to 300 μm.

10. A topical formulation according to claim 1, wherein the exine shells additionally comprise all or part of the cellulose intine layer from the naturally occurring spore.

11. A topical formulation according to claim 1, which comprises an active substance and exine shells at a weight ratio of from 0.1:1 to 33:1.

12. A topical formulation according to claim 1, wherein the exine shells are coated with a barrier layer, the barrier layer comprising a coating material which can melt, break or otherwise change on topical application so as to allow release of the active substance.

13. A topical formulation according to claim 12, wherein the coating material is solid under the normal storage conditions for the formulation, but melts at a higher temperature at which it is topically applied.

14. A topical formulation according to claim 12, wherein the barrier layer comprises a lipid coating material.

15. A product comprising a topical formulation according to claim 1.

16. A product according to claim 15, which comprises two or more substances, at least one of them being an active substance which is encapsulated within, or chemically or physically bound to, the exine shells of the naturally occurring spores.

17. A product according to claim 16, wherein the substance which is encapsulated within, or chemically or physically bound to, the exine shells is a fragrance.

18. A method for producing the topical formulation of claim 1, the method comprising (a) providing exine shells of naturally occurring spores, wherein the majority of the exine shells are at least 90% intact; and (b) encapsulating the active substance in the shell, or chemically or physically binding the active substance to the shell.

* * * * *